(12) United States Patent
Dutton et al.

(10) Patent No.: US 7,231,835 B2
(45) Date of Patent: *Jun. 19, 2007

(54) TWO-PHASE STEAM MEASUREMENT SYSTEM

(75) Inventors: Robert E. Dutton, Louisville, CO (US); Wade M. Mattar, Wrentham, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/344,046

(22) Filed: Feb. 1, 2006

(65) Prior Publication Data

US 2006/0123923 A1   Jun. 15, 2006

Related U.S. Application Data

(63) Continuation of application No. 10/737,856, filed on Dec. 18, 2003, now Pat. No. 7,013,740.

(60) Provisional application No. 60/467,553, filed on May 5, 2003.

(51) Int. Cl.
    *G01L 7/08* (2006.01)

(52) U.S. Cl. .................................. 73/861.354

(58) Field of Classification Search ............. 73/861.04, 73/861.06
    See application file for complete search history.

(56) References Cited

U.S. PATENT DOCUMENTS

| | | |
|---|---|---|
| RE31,450 E | 11/1983 | Smith |
| 4,422,338 A | 12/1983 | Smith |
| 4,491,025 A | 1/1985 | Smith et al. |
| 4,524,610 A | 6/1985 | Fitzgerald et al. |
| 4,679,947 A | 7/1987 | Miller et al. |
| 4,817,448 A | 4/1989 | Hargarten et al. |
| 4,852,395 A | 8/1989 | Kolpak |
| 4,876,897 A | 10/1989 | DeCarlo et al. |
| 4,879,911 A | 11/1989 | Zolock |

(Continued)

FOREIGN PATENT DOCUMENTS

WO    WO 02/08703    1/2002

OTHER PUBLICATIONS

Wenger, Alfred P., "Vibrating Fluid Densimeters: A Solution to the Viscosity Problem," IEEE Transactions on Industrial Electronics and Control Instrumentation, vol. 1 IECI-27, No. 3, pp. 247 253.

*Primary Examiner*—Jewel Thompson
(74) *Attorney, Agent, or Firm*—Fish & Richardson P.C.

(57) ABSTRACT

A steam measurement system includes a Coriolis flowmeter associated with a vibratable flowtube to receive a flow of wet steam. A first sensor is associated with the flowtube to relay information about a motion of the flowtube by way of a first sensor signal. A second sensor determines a property of the flow and relays the property by way of a second sensor signal. A computing device receives the first and second sensor signals and is configured to calculate a steam quality of the flow from the first and second sensor signals. The computing device also may calculate the total heat energy flow rate of the flow. Other implementations may include a full or partial separator to separate the flow of wet steam into a substantially gas flow and a substantially liquid flow and a second Coriolis meter.

18 Claims, 10 Drawing Sheets

U.S. PATENT DOCUMENTS

| | | |
|---|---|---|
| 4,911,006 A | 3/1990 | Hargarten et al. |
| 4,934,196 A | 6/1990 | Romano |
| 4,996,871 A | 3/1991 | Romano |
| 5,027,662 A | 7/1991 | Titlow et al. |
| 5,029,482 A | 7/1991 | Liu et al. |
| 5,228,327 A | 7/1993 | Bruck |
| 5,259,250 A | 11/1993 | Kolpak |
| 5,295,084 A | 3/1994 | Arunachalam et al. |
| 5,301,557 A | 4/1994 | Cage et al. |
| 5,347,874 A | 9/1994 | Kalotay et al. |
| 5,359,881 A | 11/1994 | Kalotay et al. |
| 5,398,215 A | 3/1995 | Sinha et al. |
| 5,400,653 A | 3/1995 | Kalotay |
| 5,469,748 A | 11/1995 | Kalotay |
| 5,497,666 A | 3/1996 | Patten et al. |
| 5,535,632 A | 7/1996 | Kolpak |
| 5,555,190 A | 9/1996 | Derby et al. |
| 5,594,180 A | 1/1997 | Carpenter et al. |
| 5,654,502 A | 8/1997 | Dutton |
| 5,687,100 A | 11/1997 | Buttler et al. |
| 5,734,112 A | 3/1998 | Bose et al. |
| 5,821,407 A | 10/1998 | Sekiguchi et al. |
| 5,969,264 A | 10/1999 | Rivkin |
| 6,006,609 A | 12/1999 | Drahm et al. |
| 6,032,539 A * | 3/2000 | Liu et al. ................ 73/861.04 |
| 6,092,429 A | 7/2000 | Cunningham et al. |
| 6,176,323 B1 | 1/2001 | Weirich et al. |
| 6,233,526 B1 | 5/2001 | Cunningham |
| 6,311,136 B1 | 10/2001 | Henry et al. |
| 6,318,156 B1 | 11/2001 | Dutton et al. |
| 6,318,186 B1 | 11/2001 | Smith et al. |
| 6,327,914 B1 | 12/2001 | Dutton |
| 6,343,507 B1 | 2/2002 | Felling et al. |
| 6,360,579 B1 | 3/2002 | De Boom et al. |
| 6,505,131 B1 | 1/2003 | Henrot |
| 6,505,519 B2 | 1/2003 | Henry et al. |
| 6,507,791 B2 | 1/2003 | Henry et al. |
| 6,564,619 B2 | 5/2003 | Dutton et al. |
| 6,609,067 B2 | 8/2003 | Tare et al. |
| 6,651,513 B2 | 11/2003 | Wenger et al. |
| 6,754,594 B2 | 6/2004 | Henry et al. |
| 6,758,102 B2 | 7/2004 | Henry et al. |
| 6,763,730 B1 | 7/2004 | Wray |
| 7,013,740 B2 * | 3/2006 | Dutton et al. .......... 73/861.354 |
| 2002/0033043 A1 | 3/2002 | Dutton et al. |
| 2002/0038186 A1 | 3/2002 | Henry et al. |

* cited by examiner

Table 1. Saturated Steam: Temperature Table—Continued

| Temp Fahr t | Abs Press. Lb per Sq In. p | Specific Volume Sat. Liquid $v_f$ | Specific Volume Evap $v_{fg}$ | Specific Volume Sat. Vapor $v_g$ | Enthalpy Sat. Liquid $h_f$ | Enthalpy Evap $h_{fg}$ | Enthalpy Sat. Vapor $h_g$ | Entropy Sat. Liquid $s_f$ | Entropy Evap $s_{fg}$ | Entropy Sat. Vapor $s_g$ | Temp Fahr t |
|---|---|---|---|---|---|---|---|---|---|---|---|
| 180.0 | 7.5110 | 0.016510 | 50.21 | 50.22 | 148.00 | 990.2 | 1138.2 | 0.2631 | 1.5480 | 1.8111 | 180.0 |
| 182.0 | 7.850 | 0.016522 | 48.172 | 48.189 | 150.01 | 989.0 | 1139.0 | 0.2662 | 1.5413 | 1.8075 | 182.0 |
| 184.0 | 8.203 | 0.016534 | 46.232 | 46.249 | 152.01 | 987.8 | 1139.8 | 0.2694 | 1.5346 | 1.8040 | 184.0 |
| 186.0 | 8.568 | 0.016547 | 44.383 | 44.400 | 154.02 | 986.5 | 1140.5 | 0.2725 | 1.5279 | 1.8004 | 186.0 |
| 188.0 | 8.947 | 0.016559 | 42.621 | 42.638 | 156.03 | 985.3 | 1141.3 | 0.2756 | 1.5213 | 1.7969 | 188.0 |
| 190.0 | 9.340 | 0.016572 | 40.941 | 40.957 | 158.04 | 984.1 | 1142.1 | 0.2787 | 1.5148 | 1.7934 | 190.0 |
| 192.0 | 9.747 | 0.016585 | 39.337 | 39.354 | 160.05 | 982.8 | 1142.9 | 0.2818 | 1.5082 | 1.7900 | 192.0 |
| 194.0 | 10.168 | 0.016598 | 37.808 | 37.824 | 162.05 | 981.6 | 1143.7 | 0.2848 | 1.5017 | 1.7865 | 194.0 |
| 196.0 | 10.605 | 0.016611 | 36.348 | 36.364 | 164.06 | 980.4 | 1144.4 | 0.2879 | 1.4952 | 1.7831 | 196.0 |
| 198.0 | 11.058 | 0.016624 | 34.954 | 34.970 | 166.08 | 979.1 | 1145.2 | 0.2910 | 1.4888 | 1.7798 | 198.0 |
| 200.0 | 11.526 | 0.016637 | 33.622 | 33.639 | 168.09 | 977.9 | 1146.0 | 0.2940 | 1.4824 | 1.7764 | 200.0 |
| 204.0 | 12.512 | 0.016664 | 31.135 | 31.151 | 172.11 | 975.4 | 1147.5 | 0.3001 | 1.4697 | 1.7698 | 204.0 |
| 208.0 | 13.568 | 0.016691 | 28.862 | 28.878 | 176.14 | 972.8 | 1149.0 | 0.3061 | 1.4571 | 1.7632 | 208.0 |
| 212.0 | 14.696 | 0.016719 | 26.782 | 26.799 | 180.17 | 970.3 | 1150.5 | 0.3121 | 1.4447 | 1.7568 | 212.0 |
| 216.0 | 15.901 | 0.016747 | 24.878 | 24.894 | 184.20 | 967.8 | 1152.0 | 0.3181 | 1.4323 | 1.7505 | 216.0 |
| 220.0 | 17.186 | 0.016775 | 23.131 | 23.148 | 188.23 | 965.2 | 1153.4 | 0.3241 | 1.4201 | 1.7442 | 220.0 |
| 224.0 | 18.556 | 0.016805 | 21.529 | 21.545 | 192.27 | 962.6 | 1154.9 | 0.3300 | 1.4081 | 1.7380 | 224.0 |
| 228.0 | 20.015 | 0.016834 | 20.056 | 20.073 | 196.31 | 960.0 | 1156.3 | 0.3359 | 1.3961 | 1.7320 | 228.0 |
| 232.0 | 21.567 | 0.016864 | 18.701 | 18.718 | 200.35 | 957.4 | 1157.8 | 0.3417 | 1.3842 | 1.7260 | 232.0 |
| 236.0 | 23.216 | 0.016895 | 17.454 | 17.471 | 204.40 | 954.8 | 1159.2 | 0.3476 | 1.3725 | 1.7201 | 236.0 |
| 240.0 | 24.968 | 0.016926 | 16.304 | 16.321 | 208.45 | 952.1 | 1160.6 | 0.3533 | 1.3609 | 1.7142 | 240.0 |
| 244.0 | 26.826 | 0.016958 | 15.243 | 15.260 | 212.50 | 949.5 | 1162.0 | 0.3591 | 1.3494 | 1.7085 | 244.0 |
| 248.0 | 28.796 | 0.016990 | 14.264 | 14.281 | 216.56 | 946.8 | 1163.4 | 0.3649 | 1.3379 | 1.7028 | 248.0 |
| 252.0 | 30.883 | 0.017022 | 13.358 | 13.375 | 220.62 | 944.1 | 1164.7 | 0.3706 | 1.3266 | 1.6972 | 252.0 |
| 256.0 | 33.091 | 0.017055 | 12.520 | 12.538 | 224.69 | 941.4 | 1166.1 | 0.3763 | 1.3154 | 1.6917 | 256.0 |
| 260.0 | 35.427 | 0.017089 | 11.745 | 11.762 | 228.76 | 938.6 | 1167.4 | 0.3819 | 1.3043 | 1.6862 | 260.0 |
| 264.0 | 37.894 | 0.017123 | 11.025 | 11.042 | 232.83 | 935.9 | 1168.7 | 0.3876 | 1.2933 | 1.6808 | 264.0 |
| 268.0 | 40.500 | 0.017157 | 10.358 | 10.375 | 236.91 | 933.1 | 1170.0 | 0.3932 | 1.2823 | 1.6755 | 268.0 |
| 272.0 | 43.249 | 0.017193 | 9.738 | 9.755 | 240.99 | 930.3 | 1171.3 | 0.3987 | 1.2715 | 1.6702 | 272.0 |
| 276.0 | 46.147 | 0.017228 | 9.162 | 9.180 | 245.08 | 927.5 | 1172.5 | 0.4043 | 1.2607 | 1.6650 | 276.0 |
| 280.0 | 49.200 | 0.017264 | 8.627 | 8.644 | 249.17 | 924.6 | 1173.8 | 0.4098 | 1.2501 | 1.6599 | 280.0 |
| 284.0 | 52.414 | 0.01730 | 8.1280 | 8.1453 | 253.3 | 921.7 | 1175.0 | 0.4154 | 1.2395 | 1.6548 | 284.0 |
| 288.0 | 55.795 | 0.01734 | 7.6634 | 7.6807 | 257.4 | 918.8 | 1176.2 | 0.4208 | 1.2290 | 1.6498 | 288.0 |
| 292.0 | 59.350 | 0.01738 | 7.2301 | 7.2475 | 261.5 | 915.9 | 1177.4 | 0.4263 | 1.2186 | 1.6449 | 292.0 |
| 296.0 | 63.084 | 0.01741 | 6.8259 | 6.8433 | 265.6 | 913.0 | 1178.6 | 0.4317 | 1.2082 | 1.6400 | 296.0 |
| 300.0 | 67.005 | 0.01745 | 6.4483 | 6.4658 | 269.7 | 910.0 | 1179.7 | 0.4372 | 1.1979 | 1.6351 | 300.0 |
| 304.0 | 71.119 | 0.01749 | 6.0955 | 6.1130 | 273.8 | 907.0 | 1180.9 | 0.4426 | 1.1877 | 1.6303 | 304.0 |
| 308.0 | 75.433 | 0.01753 | 5.7655 | 5.7830 | 278.0 | 904.0 | 1182.0 | 0.4479 | 1.1776 | 1.6256 | 308.0 |
| 312.0 | 79.953 | 0.01757 | 5.4566 | 5.4742 | 282.1 | 901.0 | 1183.1 | 0.4533 | 1.1676 | 1.6209 | 312.0 |
| 316.0 | 84.688 | 0.01761 | 5.1673 | 5.1849 | 286.3 | 897.9 | 1184.1 | 0.4586 | 1.1576 | 1.6162 | 316.0 |
| 320.0 | 89.643 | 0.01766 | 4.8961 | 4.9138 | 290.4 | 894.8 | 1185.2 | 0.4640 | 1.1477 | 1.6116 | 320.0 |
| 324.0 | 94.826 | 0.01770 | 4.6418 | 4.6595 | 294.6 | 891.6 | 1186.2 | 0.4692 | 1.1378 | 1.6071 | 324.0 |
| 328.0 | 100.245 | 0.01774 | 4.4030 | 4.4208 | 298.7 | 888.5 | 1187.2 | 0.4745 | 1.1280 | 1.6025 | 328.0 |
| 332.0 | 105.907 | 0.01779 | 4.1788 | 4.1966 | 302.9 | 885.3 | 1188.2 | 0.4798 | 1.1183 | 1.5981 | 332.0 |
| 336.0 | 111.820 | 0.01783 | 3.9681 | 3.9859 | 307.1 | 882.1 | 1189.1 | 0.4850 | 1.1086 | 1.5936 | 336.0 |
| 340.0 | 117.992 | 0.01787 | 3.7699 | 3.7878 | 311.3 | 878.8 | 1190.1 | 0.4902 | 1.0990 | 1.5892 | 340.0 |
| 344.0 | 124.430 | 0.01792 | 3.5834 | 3.6013 | 315.5 | 875.5 | 1191.0 | 0.4954 | 1.0894 | 1.5849 | 344.0 |
| 348.0 | 131.142 | 0.01797 | 3.4078 | 3.4258 | 319.7 | 872.2 | 1191.1 | 0.5006 | 1.0799 | 1.5806 | 348.0 |
| 352.0 | 138.138 | 0.01801 | 3.2423 | 3.2603 | 323.9 | 868.9 | 1192.7 | 0.5058 | 1.0705 | 1.5763 | 352.0 |
| 356.0 | 145.424 | 0.01806 | 3.0863 | 3.1044 | 328.1 | 865.5 | 1193.6 | 0.5110 | 1.0611 | 1.5721 | 356.0 |
| → 360.0 | 153.010 | 0.01811 | 2.9392 | 2.9573 | 332.3 | 862.1 | 1194.4 | 0.5161 | 1.0517 | 1.5678 | 360.0 |
| 364.0 | 160.903 | 0.01816 | 2.8002 | 2.8184 | 336.5 | 858.6 | 1195.2 | 0.5212 | 1.0424 | 1.5637 | 364.0 |
| 368.0 | 169.113 | 0.01821 | 2.6691 | 2.6873 | 340.8 | 855.1 | 1195.9 | 0.5263 | 1.0332 | 1.5595 | 368.0 |
| 372.0 | 177.648 | 0.01826 | 2.5451 | 2.5633 | 345.0 | 851.6 | 1196.7 | 0.5314 | 1.0240 | 1.5554 | 372.0 |
| 376.0 | 186.517 | 0.01831 | 2.4279 | 2.4462 | 349.3 | 848.1 | 1197.4 | 0.5365 | 1.0148 | 1.5513 | 376.0 |
| 380.0 | 195.729 | 0.01836 | 2.3170 | 2.3353 | 353.6 | 844.5 | 1198.0 | 0.5416 | 1.0057 | 1.5473 | 380.0 |
| 384.0 | 205.294 | 0.01842 | 2.2120 | 2.2304 | 357.9 | 840.8 | 1198.7 | 0.5466 | 0.9966 | 1.5432 | 384.0 |
| 388.0 | 215.220 | 0.01847 | 2.1126 | 2.1311 | 362.2 | 837.2 | 1199.3 | 0.5516 | 0.9876 | 1.5392 | 388.0 |
| 392.0 | 225.516 | 0.01853 | 2.0184 | 2.0369 | 366.5 | 833.4 | 1199.9 | 0.5567 | 0.9786 | 1.5352 | 392.0 |
| 396.0 | 236.193 | 0.01858 | 1.9291 | 1.9477 | 370.8 | 829.7 | 1200.4 | 0.5617 | 0.9696 | 1.5313 | 396.0 |
| 400.0 | 247.259 | 0.01864 | 1.8444 | 1.8630 | 375.1 | 825.9 | 1201.0 | 0.5667 | 0.9607 | 1.5274 | 400.0 |
| 404.0 | 258.725 | 0.01870 | 1.7640 | 1.7827 | 379.4 | 822.0 | 1201.5 | 0.5717 | 0.9518 | 1.5234 | 404.0 |
| 408.0 | 270.600 | 0.01875 | 1.6877 | 1.7064 | 383.8 | 818.2 | 1201.9 | 0.5766 | 0.9429 | 1.5195 | 408.0 |
| 412.0 | 282.894 | 0.01881 | 1.6152 | 1.6349 | 388.1 | 814.2 | 1202.4 | 0.5816 | 0.9341 | 1.5157 | 412.0 |
| 416.0 | 295.617 | 0.01887 | 1.5463 | 1.5651 | 392.5 | 810.2 | 1202.8 | 0.5866 | 0.9253 | 1.5118 | 416.0 |
| 420.0 | 308.780 | 0.01894 | 1.4808 | 1.4997 | 396.9 | 806.2 | 1203.1 | 0.5915 | 0.9165 | 1.5080 | 420.0 |
| 424.0 | 322.391 | 0.01900 | 1.4184 | 1.4374 | 401.3 | 802.2 | 1203.5 | 0.5964 | 0.9077 | 1.5042 | 424.0 |
| 428.0 | 336.463 | 0.01906 | 1.3591 | 1.3782 | 405.7 | 798.0 | 1203.7 | 0.6014 | 0.8990 | 1.5004 | 428.0 |
| 432.0 | 351.00 | 0.01913 | 1.30266 | 1.32179 | 410.1 | 793.9 | 1204.0 | 0.6063 | 0.8903 | 1.4966 | 432.0 |
| 436.0 | 366.03 | 0.01919 | 1.24887 | 1.26806 | 414.6 | 789.7 | 1204.2 | 0.6112 | 0.8816 | 1.4928 | 436.0 |
| → 440.0 | 381.54 | 0.01926 | 1.19761 | 1.21687 | 419.0 | 785.4 | 1204.4 | 0.6161 | 0.8729 | 1.4890 | 440.0 |
| 444.0 | 397.56 | 0.01933 | 1.14874 | 1.16806 | 423.5 | 781.2 | 1204.6 | 0.6210 | 0.8643 | 1.4853 | 444.0 |
| 448.0 | 414.09 | 0.01940 | 1.10212 | 1.12152 | 428.0 | 776.7 | 1204.7 | 0.6259 | 0.8557 | 1.4815 | 448.0 |
| 452.0 | 431.14 | 0.01947 | 1.05764 | 1.07711 | 432.5 | 772.3 | 1204.8 | 0.6308 | 0.8471 | 1.4778 | 452.0 |
| 456.0 | 448.73 | 0.01954 | 1.01518 | 1.03472 | 437.0 | 767.8 | 1204.8 | 0.6356 | 0.8385 | 1.4741 | 456.0 |

FIG. 3

TWO-PHASE STEAM MEASUREMENT SYSTEM

CLAIM OF PRIORITY

This application is a continuation of U.S. application Ser. No. 10/737,856, filed Dec. 18, 2003 now U.S. Pat. No. 7,013,740 and titled "Two-Phase Steam Measurement System," which claims priority under 35 USC §119(e) to U.S. Patent Application Ser. No. 60/467,553, filed on May 5, 2003, both of which are hereby incorporated by reference.

TECHNICAL FIELD

This description relates to two-phase steam measurements.

BACKGROUND

There are instances in which it is beneficial to measure various properties of saturated steam. One such instance is the extraction of crude oil from the ground. Heavy, tar-like oil lies in geologic formations below the earth's surface in large quantities. In order to extract this commercially valuable resource, wet, saturated steam may be produced at a steam generator or other steam-producing device and transported through various transport elements (such as, for example, flow lines, manifolds, valves, tees, and fittings) to one or more injection wells at the site(s) of the heavy, tar-like oil. At the injection wells, the steam may be injected into the heavy oil formations to thin the crude oil and facilitate pumping it to the surface.

SUMMARY

In one aspect, a steam measurement system is provided. The steam measurement system includes a Coriolis flowtube to receive a flow of wet steam. A bulk density of the flow is determined based on a motion of the Coriolis flowtube. A sensor determines a property of the flow of wet steam. A computing device calculates a steam quality of the flow from the bulk density and the property.

Implementations of this aspect may include one or more of the following features. For example, the property may be a temperature of the flow, with the sensor being a temperature sensor. The temperature sensor may be connected to the outside of the flowtube or the temperature sensor may be inserted into the flow of wet steam. The property may be a pressure of the flow, with the sensor being a pressure sensor.

To calculate the steam quality, the computing device may be configured to calculate a density of a vapor phase of the flow from the property and to calculate a density of a liquid phase of the flow from the property. The computing device may include a memory storing a steam table and be configured to use the steam table to calculate the density of the vapor phase from the property and the density of the liquid phase from the property. The computing device may be configured to calculate the steam quality using the bulk density, the density of the liquid phase, and the density of the gas phase to by solving the following equation for the steam quality x:

$$\frac{1}{\text{Bulk Density}} = \frac{x}{\text{Vapor Density}} + \frac{1-x}{\text{Liquid Density}}.$$

The computing device also may be configured to determine a bulk mass flow rate of the flow based on a motion of the Coriolis flowtube and may be configured to calculate a heat energy flow rate of the flow from the steam quality and the bulk mass flow rate. To calculate the heat energy flow rate, the computing device may be configured to calculate an enthalpy of the vapor phase of the flow from the property, to calculate an enthalpy of the liquid phase of the flow from the property. The computing device may be configured to calculate the heat energy flow rate using the bulk mass flow rate m, the enthalpy of the liquid phase $h_f$, the enthalpy of the gas phase $h_g$, and the steam quality x by solving the following equation for the heat energy flow rate $H_{total}$:

$$H_{total} = m \cdot h_g \cdot x + m \cdot h_f \cdot (1-x).$$

The computing device may be a Coriolis flowmeter transmitter or a flow computer.

The steam measurement system also may include a steam generator to generate the flow of wet steam; a transport element to deliver the flow of wet steam to the Coriolis flowtube; and an injection well connected to the Coriolis flowtube to receive the flow of wet steam from the Coriolis flowtube.

In another aspect, a method is provided that includes passing a flow of wet steam through a vibrating flowtube associated with a Coriolis flowmeter, wherein the Coriolis flowmeter determines the bulk density of the flow of wet steam; obtaining a temperature or a pressure of the flow of wet steam; and calculating a steam quality of the flow from the bulk density and the temperature or pressure.

Implementations of this aspect may include one or more of the following features. For example, calculating the steam quality may include calculating a density of a vapor phase of the flow from the temperature or pressure; and calculating a density of a liquid phase of the flow from the temperature or pressure. The steam quality may be calculated by solving the following equation for the steam quality x:

$$\frac{1}{\text{Bulk Density}} = \frac{x}{\text{Vapor Density}} + \frac{1-x}{\text{Liquid Density}}.$$

The bulk mass flow rate of the flow may be calculated and a heat energy flow rate of the flow also may be calculated from the steam quality, the bulk mass flow rate, and the temperature or pressure. Calculating the heat energy flow rate may include calculating an enthalpy of the vapor phase of the flow from the temperature or pressure; and calculating an enthalpy of the liquid phase of the flow from the temperature or pressure. The heat energy flow rate $H_{total}$ may be calculated by solving the following equation:

$$H_{total} = m \cdot h_g \cdot x + m \cdot h_f \cdot (1-x),$$

where m is the bulk mass flow rate, $h_f$ is the enthalpy of the liquid phase, $h_g$ is the enthalpy of the gas phase, and x is the steam quality.

In another aspect, a steam measurement system including a separator is provided. The separator separates a flow of wet steam into a substantially gas flow and a substantially liquid flow. A first Coriolis flowtube receives the substantially gas flow and a bulk density of the substantially gas flow is calculated based on a motion of the first Coriolis flowtube. A second Coriolis flowtube receives the substantially liquid flow and a bulk density of the substantially liquid flow is determined based on a motion of the second Coriolis flowtube. A sensor detects a temperature or pressure of the substantially gas flow or the substantially liquid flow. A computing device is configured to calculate a total steam quality of the flow of wet steam from the bulk density of the substantially gas flow, the bulk density of the substantially liquid flow, and the temperature or pressure.

Implementations of this aspect may include one or more of the following features. For example, the sensor may be a temperature sensor. The temperature sensor may be connected to the outside of the first or second Coriolis flowtube or inserted into the substantially gas or substantially liquid flow. The sensor may be a pressure sensor.

To calculate the steam quality, the computing device may be configured to use the temperature or pressure to calculate a density of a vapor phase of the substantially gas flow; a density of a liquid phase of the substantially gas flow; a density of a vapor phase of the substantially liquid flow; and a density of a liquid phase of the substantially liquid flow. The computing device may include a memory storing a steam table and be configured to use the steam table to calculate the density of a vapor phase of the substantially gas flow; the density of a liquid phase of the substantially gas flow; the density of a vapor phase of the substantially liquid flow; and the density of a liquid phase of the substantially liquid flow.

A bulk mass flowrate of the substantially gas flow may be determined based on motion information of the first Coriolis flowtube and a bulk mass flowrate of the substantially liquid flow may be determined based on motion information of the second Coriolis flowtube. The computing device may be configured to calculate a heat energy flow rate of the flow from the steam quality, the bulk mass flowrate of the substantially liquid flow, the bulk mass flowrate of the substantially gas flow, and the temperature or pressure.

To calculate the heat energy flow rate, the computing device may be configured to use the temperature or pressure to calculate an enthalpy of the vapor phase of the substantially gas flow; to calculate an enthalpy of the liquid phase of the substantially gas flow; to calculate an enthalpy of the vapor phase of the substantially liquid flow; and to calculate an enthalpy of the liquid phase of the substantially liquid flow. The computing device may be a Coriolis flowmeter transmitter or a flow computer.

The steam measurement system also may include a steam generator to generate the flow of wet steam; a transport element to deliver the flow of wet steam to the separator; and an injection well connected to the first and second Coriolis flowtubes to receive the substantially gas and substantially liquid flows from the first and second Coriolis flowtubes.

In another aspect, a Coriolis transmitter for use with a steam measurement system includes a Coriolis flowtube to receive a flow of wet steam; a first sensor associated with the flowtube to relay information about a motion of the flowtube by way of a first sensor signal; and a second sensor to determine a property of the flow and to relay the property by way of a second sensor signal. The Coriolis transmitter includes a processing device to receive the first and second sensor signals. The processing device is configured to calculate a steam quality of the flow from the first and second sensor signals.

Implementations of this aspect may include one or more of the following features. For example, the processing device also may be configured to calculate a heat energy flow rate of the flow from the steam quality and the first and second sensor signals. To calculate the heat energy flow rate, the processing device may be configured to calculate an enthalpy of the vapor phase of the flow from the property, to calculate an enthalpy of the liquid phase of the flow from the property, and to calculate a bulk mass flowrate of the flow from the first sensor signal. The processing device may be configured to calculate the heat energy flow rate using the bulk mass flow rate m, the enthalpy of the liquid phase $h_f$, the enthalpy of the gas phase $h_g$, and the steam quality x by solving the following equation for the heat energy flow rate $H_{total}$:

$$H_{total} = m \cdot h_g \cdot x + m \cdot h_f \cdot (1-x).$$

The details of one or more implementations are set forth in the accompanying drawings and the description below. Other features will be apparent from the description and drawings, and from the claims.

DESCRIPTION OF DRAWINGS

FIG. 3 is an excerpt from a saturated steam temperature table.

DETAILED DESCRIPTION

Figure 1:
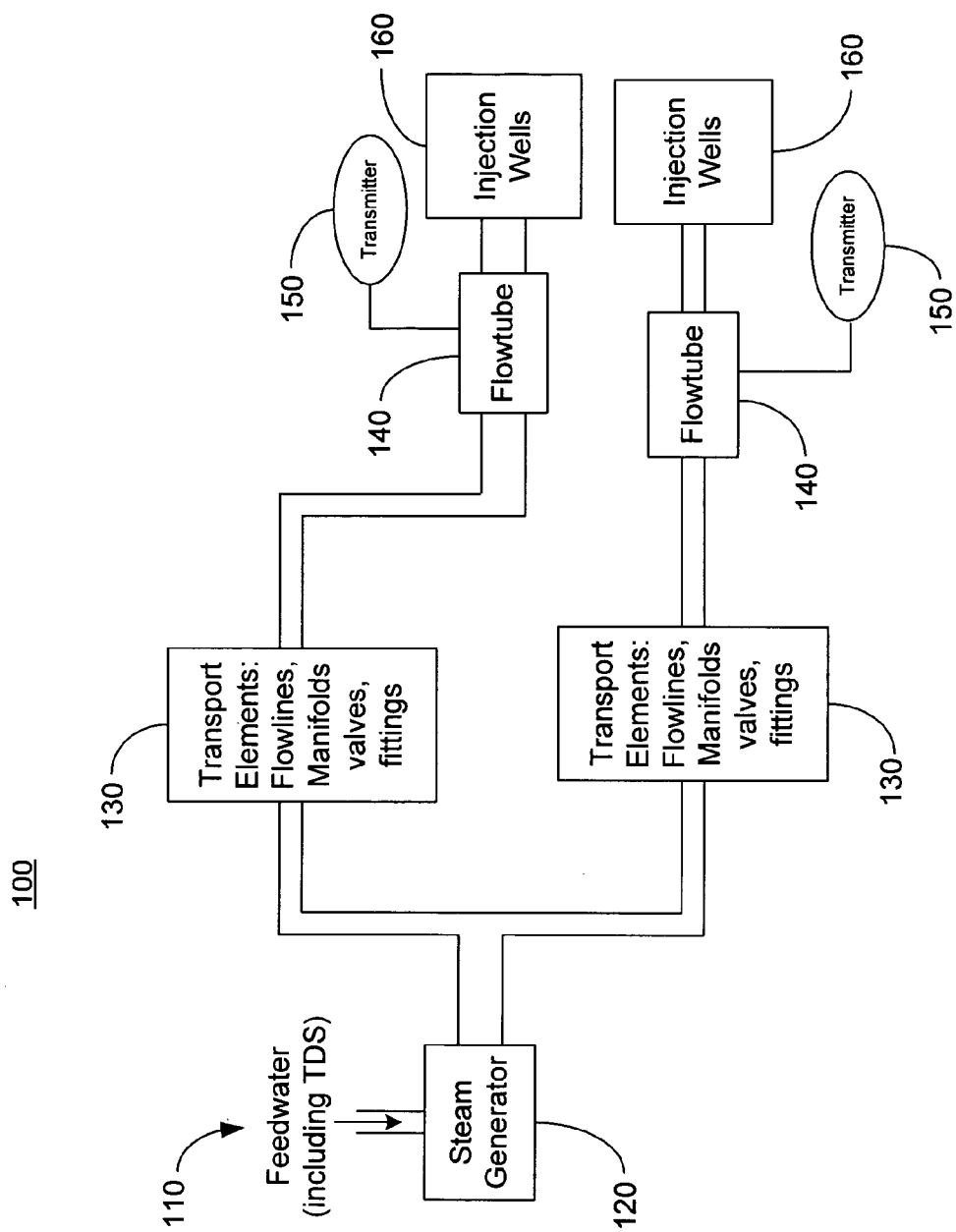
FIG. 1 is a block diagram of a two-phase steam measurement system used at injection wells.

FIG. 1 is a block diagram of a steam generation and injection system 100 that includes a two-phase steam measurement system. System 100 includes a steam generator 120, transport elements 130 connecting the output of steam generator 120 to injection wells 160, and meters 140 along with corresponding transmitters 150 located near the injection wells. In general, feedwater 110 is input to steam generator 120, which turns feedwater 110 into steam. The steam is transported to the injection wells 160 by transport elements 130, e.g. flowlines, manifolds, valves and fittings. Meters 140, along with the corresponding transmitters 150, are used to measure properties of the steam near injection wells 160.

Feedwater 110 may be distilled to remove any solids or other impurities. However, using distilled water may be expensive or impractical. Alternatively, oil companies may produce steam in steam generators rather than other steam-producing equipment, such as boilers, so that, for example, enough liquid leaves the steam generator to carry away any dissolved solids that may exist in the feedwater used by the steam generator in generating the steam. This eliminates the expensive proposition of using distilled water as the feedwater. Thus, the steam produced and transported is typically "wet steam," i.e., water with a phase relationship such that liquid is contained in some form or amount within a vapor of the water.

Figure 2:
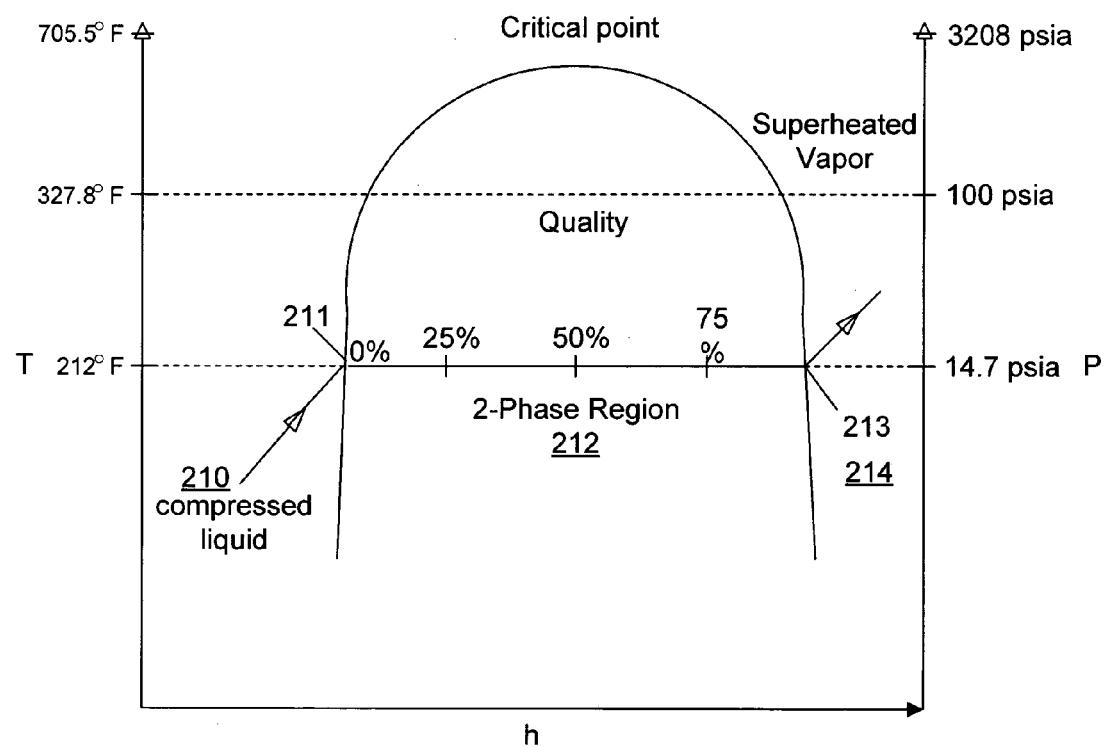
FIG. 2 is a diagram illustrating a temperature-pressure relationship of water.

FIG. 2 is a phase diagram 200 illustrating the two-phase nature of a pure substance, in this case water. As shown in FIG. 2, a temperature and/or pressure of water determines state characteristics of the water. For example, the water might be in a compressed liquid state 210, but as heat is added, the temperature of the compressed liquid rises until it reaches the saturation liquid line 211. If this is done at atmospheric pressure then the temperature is 212° F. If heat is continuously added to the water at atmospheric pressure, some of the liquid turns to vapor. If enough heat is added to convert half, by mass, of the liquid to vapor for example, then the steam is said to have 50% quality. As we continue to add heat to the steam, all of the liquid turns to vapor at the saturation vapor line 213. At this point the temperature is still 212° F. and the pressure is still one atmosphere absolute. If heat is further applied to this steam, the temperature and pressure will rise into the superheated vapor state 214, where the temperature and pressure are independent of one another.

Thus the term wet/saturated steam is a thermodynamic term, meaning water that is not superheated nor compressed liquid, and is below the critical point of 705.5° F. and 3208 psia. Saturated steam can be from 0% to 100% in "steam quality," as discussed below, and its temperature and pressure are related in the Two-Phase Region 212 of the phase diagram 200. For instance, 212° F. is tied to atmospheric pressure of 14.7 psia, as is 327.8° F. is tied to 100 psia. Steam tables have been developed to give the properties of saturated steam (e.g., density and heat energy of the phases) at a given temperature and corresponding pressure.

FIG. 3 is an excerpt from a saturated steam temperature table. As just described, such a table relates various properties associated with water at various conditions. Specifically, the table of FIG. 3 illustrates various properties of wet/saturated steam at various temperatures and pressures. The properties include the specific volume of the components of the wet steam (specific volume represents the space occupied per unit mass of a substance, and is the mathematical inverse of density), the enthalpy of the components of the wet steam (i.e., a term that represents the total energy content of the wet steam; it expresses the internal energy and flow work, or the total potential energy and kinetic energy contained within a substance, and may be expressed in, for example, British thermal units per pound (mass), or BTU/lbm), and the entropy of the components of the wet steam (representing, in this case, energy of the wet steam that may be lost due to transportation of the wet steam).

Wet steam that leaves generator 120 is said to have a particular "steam quality," which refers to the percentage of the steam, by mass, that is in the vapor phase. For example, wet steam that is 80% vapor may be said to have an 80% steam quality. The remainder of the saturated steam is in the liquid phase, and it carries away the dissolved solids so that, for example, the heat exchange tubes of steam generator 120 do not become coated and fail.

As described previously, this wet/saturated steam leaves steam generator 120 and flows through transport elements 130 on its way to injection wells 160, as shown in FIG. 1. These transport elements 130 may lie over various topographical formations. For example, some transport elements 130 may traverse hills and have a high elevation, whereas other transport elements 130 may lie in valleys and have a low elevation. As the steam flow splits and divides and traverses the various transport elements 130 in their various settings, the liquid does not always remain with the vapor in the same ratio that it left generator 120. As a result, the quality of the steam flows that reach injection wells 160 may be significantly different from one another and from the quality of the steam when exiting the steam generators, and may range anywhere from 0% to 100%. Capacitance probes, dual orifice plates, and vibrating tube densitometers, for example, have been used in the past to try to measure this steam quality, with very limited success.

Knowledge of the steam quality at the injection wells 160, as opposed to at the generator 120, may be important to operators of injection wells 160. For example, the operators may want to know the steam quality at injection wells 160 because the steam quality often is related to the amount of commercially-usable oil that is extracted. In particular, when more vapor is contained within the wet steam (i.e., when the steam quality is high), more energy may be transferred into injection wells 160. Therefore, operators of injection wells 160 may seek to optimize steam flow into injection wells 160, so as to extract a maximized amount of oil relative to a minimized amount of wet steam injected into wells 160.

This optimization process may include, for example, using flowtubes 140 and corresponding transmitters 150 to detect a low steam quality at a particular injection well and fixing a flow fault that is associated with transport elements 130 (and/or with steam generator 120) associated with that well. The optimization process also may include, as another example, adjusting various transport elements 130 to ensure that the various injection wells 160 do not receive significantly different steam qualities.

Flowtubes 140 and corresponding transmitters 150 are, respectively, Coriolis flowtubes and Coriolis transmitters. A Coriolis flowtube and Coriolis transmitter are collectively referred to as a Coriolis flowmeter. A Coriolis flowmeter is a type of flowmeter, where flowmeters, generally speaking, provide information about materials being transferred through a conduit or flowtube. For example, density meters, or densitometers, provide a measurement of the density of material flowing through a conduit. Additionally, mass flowmeters provide a measurement of the mass of material being transferred through a conduit by, for example, deriving the mass flow measurement from an earlier density measurement and a volumetric flow measurement. Other mass flowmeters may calculate mass flow directly.

Coriolis-type flowmeter systems calculate density and mass flow using the Coriolis effect, in which material flowing through a rotating conduit becomes a radially-traveling mass that is affected by a Coriolis force and therefore experiences an acceleration. Many Coriolis mass flowmeter systems induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

In general, the term flowtube as used herein refers to the flowtube and any associated mechanical parts, drivers, and sensors, while the term "transmitter" refers to the electronics for producing drive signals to control the flowtube oscillations and calculating the properties of the material flowing through the flowtube based on signals received from the sensors. Additionally, the term Coriolis flowmeter generally refers to a combination of flowtube and transmitter.

U.S. Pat. No. 6,311,136 and U.S. Pat. No. 6,507,791, which are hereby incorporated by reference, disclose the use of a digital flowmeter system and related technology. Such digital flowmeter systems are very precise in their measurements, with little or negligible noise, and are capable of enabling a wide range of positive and negative gains at the driver circuitry for driving the conduit. Such digital flowmeter systems are thus advantageous in a variety of settings. For example, U.S. Pat. No. 6,505,519 discloses the use of a wide gain range, and/or the use of negative gain, to prevent stalling and to more accurately exercise control of the flowtube, even during difficult conditions such as the two-phase flow of wet/saturated steam.

A digital transmitter exchanges sensor and drive signals with its associated conduit or flowtube, so as to both sense an oscillation of the flowtube, and to drive the oscillation of the flowtube accordingly. By quickly and accurately determining the sensor and drive signals, the digital transmitter may provide for fast and accurate operation of the flowtube in determining characteristics of the flow including a mass flow rate of the flow. A digital transmitter may be implemented using one or more of, for example, a processor, a field-programmable gate array, an ASIC, other programmable logic or gate arrays, or programmable logic with a processor core.

Although digital flowmeter systems are discussed above, it should be understood that analog Coriolis flowmeter systems also exist. Although such analog flowmeter systems may be prone to typical shortcomings of analog circuitry, e.g., low precision and high noise measurements relative to digital flowmeters, they also may be compatible with the various techniques and implementations discussed herein. Thus, the terms "flowtube," "transmitter," and "flowmeter" should not be understood as being limited to digital systems.

Figure 4:
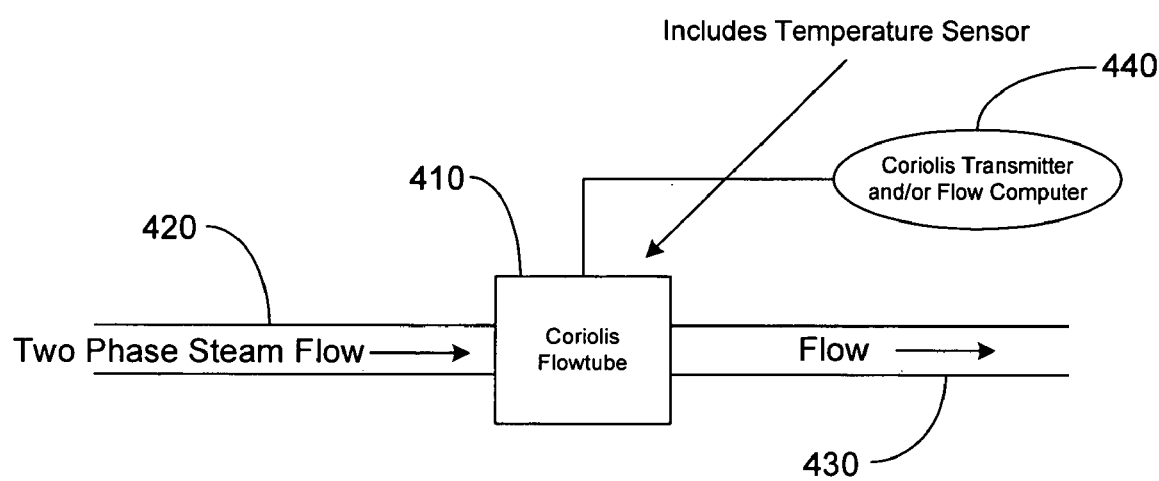
FIG. 4 is a block diagram of a Coriolis meter being used in a steam measurement system.
Figure 5:
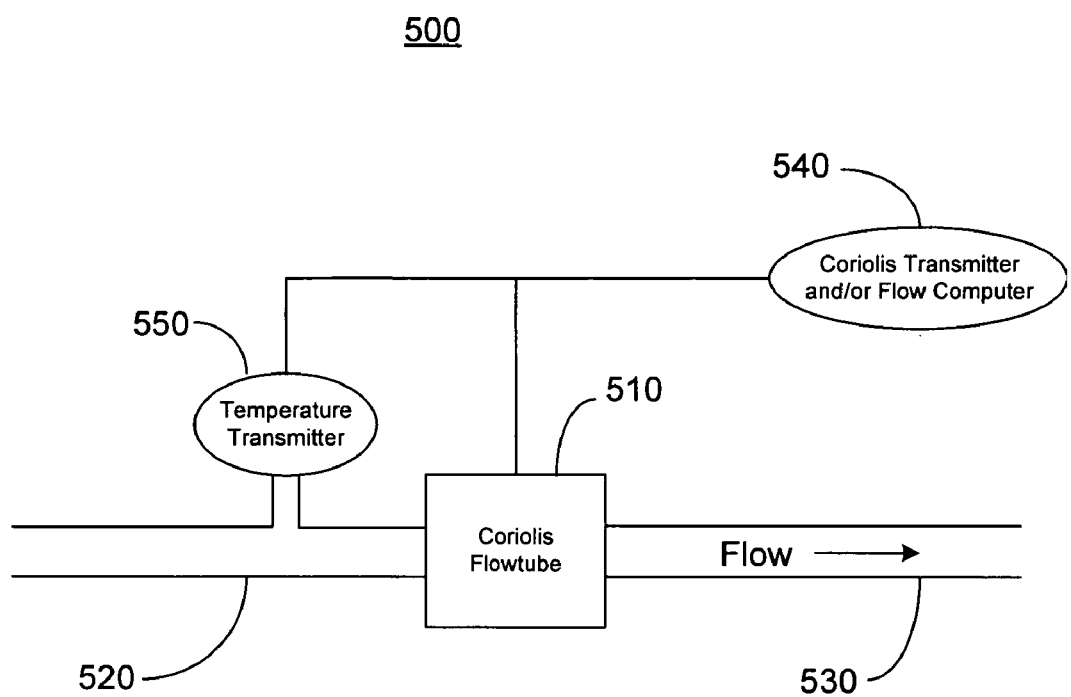
FIG. 5 is a block diagram of a Coriolis meter and a temperature transmitter being used in a steam measurement system.
Figure 6:
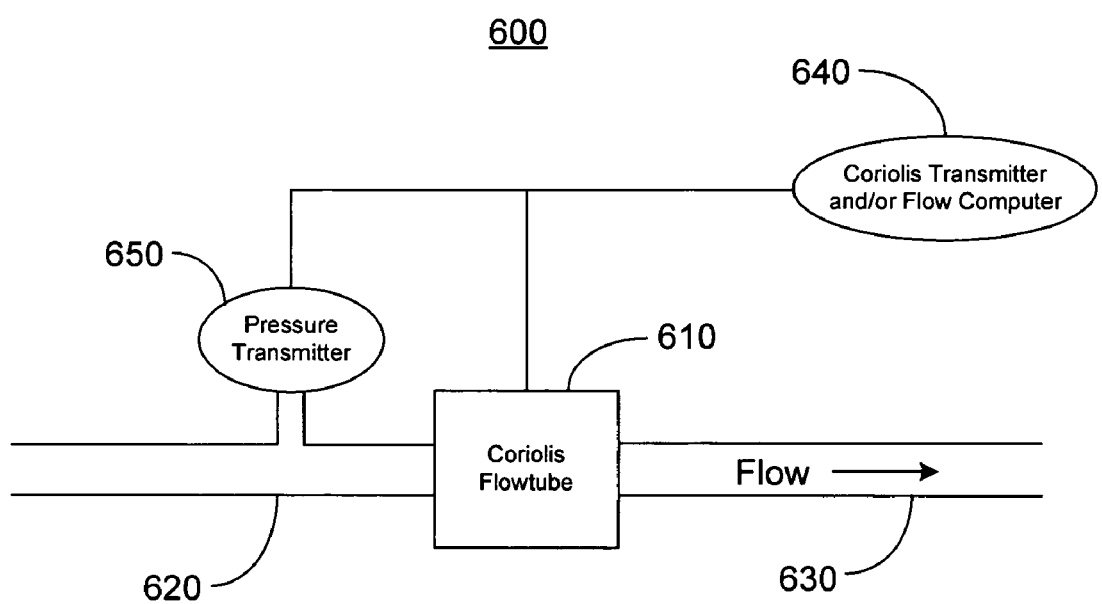
FIG. 6 is a block diagram of a Coriolis meter and a pressure transmitter being used in a steam measurement system.

FIGS. 4-6 illustrate various configurations in which a Coriolis flowmeter and other sensors may be used to measure steam quality and/or other properties of wet steam, for example, near an injection well. In general, by measuring the bulk density of the wet steam using the Coriolis flowmeter along with a measurement of the wet steam's temperature or pressure, the steam quality and other properties of the wet steam may be determined.

FIG. 4 is a block diagram illustrating a Coriolis flowmeter system used in a steam measurement system 400. System 400 includes a Coriolis flowtube 410 that receives wet steam from an input transport element 420. After flowing through the flowtube 410, the wet steam exits through an output transport element 430. As the wet steam flows through the flowtube 410, various measurements of the flowtube 410 are taken so that a Coriolis transmitter 440 can determine the bulk density of the wet steam. In addition, a temperature sensor is associated with the Coriolis flowtube 410 and coupled to the flowtube 410 to obtain flowtube temperature data, which is indicative of the temperature of the wet steam. For example, a resistance temperature device (RTD) may be coupled to the flowtube 410 and used to obtain flowtube temperature data.

The temperature sensor may be one that is provided with Coriolis flowtube 410 to correct for temperature changes of the flowtube 410. Specifically, in some Coriolis flowmeters, a temperature sensor is already associated with the Coriolis flowtube because a temperature of the flowtube and/or the material being transported may affect, for example, a stiffness of the flowtube (and thereby a resonant frequency of oscillation of the flowtube, which, in turn, may affect a density and/or mass flow measurement obtained by the flowmeter). Alternatively, the temperature sensor coupled to the flowtube may be used solely for a temperature measurement related to the measurement of properties of the wet steam.

By using the temperature of the flowtube 410 (and, indirectly, of the wet steam) thus obtained, along with the information contained in a steam table such as that shown in FIG. 3 and the bulk density of the wet steam as measured by the Coriolis flowmeter, the steam quality and other properties of the flow may be calculated in the manner(s) described below with respect to FIG. 7. These calculations may be performed by transmitter 440 and/or may be performed by an associated flow computer 440, such as might be used to measure the oil and oil-mixtures produced. Such flow computers may be used in conjunction with multiple wells and/or multiple steam quality calculations at those (or other) wells. The calculations also may be performed, for example, by a programmed control system.

FIG. 5 is a block diagram of a Coriolis flowtube 510 and a separate temperature transmitter 550 used in a steam measurement system 500. System 500 is similar to system 400 except for a separate temperature transmitter/sensor 550 is used in addition, or as an alternative, to a temperature sensor associated with Coriolis flowtube 510. Temperature transmitter 550 may include a thermal well or temperature probe inserted into the flowing material (i.e., wet steam) itself. Temperature transmitter 550, particularly if calibrated before being put into the flow, may provide a more accurate measure of the temperature of the wet steam (particularly because it is directly measuring the wet steam itself, and is not indirectly determining the temperature of the wet steam based on a temperature of the flowtube obtained by an external sensor, such as in FIG. 4).

FIG. 6 is a block diagram of a Coriolis flowtube 610 and a pressure transmitter 650 used in a steam measurement system 600. System 600 is similar to system 500 except for a pressure transmitter/sensor 650 is used in place of a temperature transmitter/sensor 550. As described above, temperature and pressure are tied together for wet steam. Thus, either pressure or temperature provides the information necessary to calculate the steam quality or other properties as described below.

Figure 7:
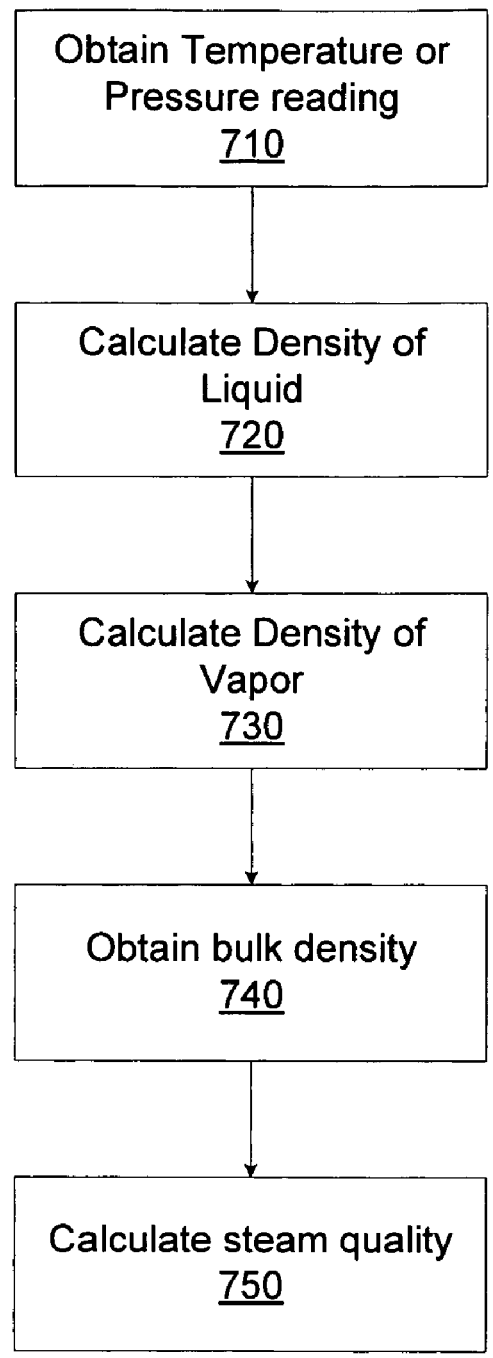
FIG. 7 is a flowchart describing a process for determining steam quality measurements.

FIG. 7 is a flowchart illustrating a process for determining steam quality measurements using a system such as one of those shown in FIGS. 4-6. A temperature or pressure reading of the steam is obtained (710) from a temperature or pressure sensor/transmitter, such as sensor 550 or 650. The temperature or pressure is then used to calculate the density of the liquid phase (720) and the density of the vapor phase (730).

The densities may be calculated by storing a steam table, for example, in a transmitter and looking up the appropriate property in the steam table. For instance, referring to the steam table of FIG. 3, if the temperature sensor associated with Coriolis meter 410 or temperature transmitter 550 indicates 360° F. (or if absolute pressure transmitter 650 indicates 153 psia) then the density of the liquid phase (as the inverse of specific volume $v_f$) is calculated from the steam table of FIG. 3 as:

$$\frac{1}{v_f} = \frac{1}{0.01811} = 55.22 \text{ lb/ft}^3$$

and the density of the vapor phase (as the inverse of specific volume $v_g$) is calculated from the steam table of FIG. 3 as:

$$\frac{1}{v_g} = \frac{1}{2.9573} = 0.3381 \text{ lb/ft}^3$$

Alternatively, the steam table information may be stored algorithmically and the algorithm may be used to obtain the densities.

The bulk density of the wet steam flowing through the flowtube is obtained (740). The densities of the vapor and liquid phases, along with the bulk density are then used to calculate the steam quality (750). The following equation expresses the relationship between the bulk density, vapor density, liquid density, and steam quality x.

$$\frac{1}{\text{Bulk Density}} = \frac{x}{\text{Vapor Density}} + \frac{1-x}{\text{Liquid Density}}$$

The steam quality thus can be determined by solving for x, given the bulk density, liquid density, and vapor density. To continue the example from above, if the bulk density is, for example, 0.5 lb/ft$^3$, then the steam quality is calculated as:

$$\frac{1}{0.5} = \frac{x}{0.3381} + \frac{1-x}{55.22}$$

$x = 0.67$ or 67% steam quality.

In short, a Coriolis flowmeter (and/or a temperature/pressure sensor) can be used with a table such as the one of FIG. 3 to determine a density of each of the gas and liquid phases of the wet steam. Since the Coriolis meter may measure the bulk density, the steam quality may be deduced in the manner just described.

Figure 8:
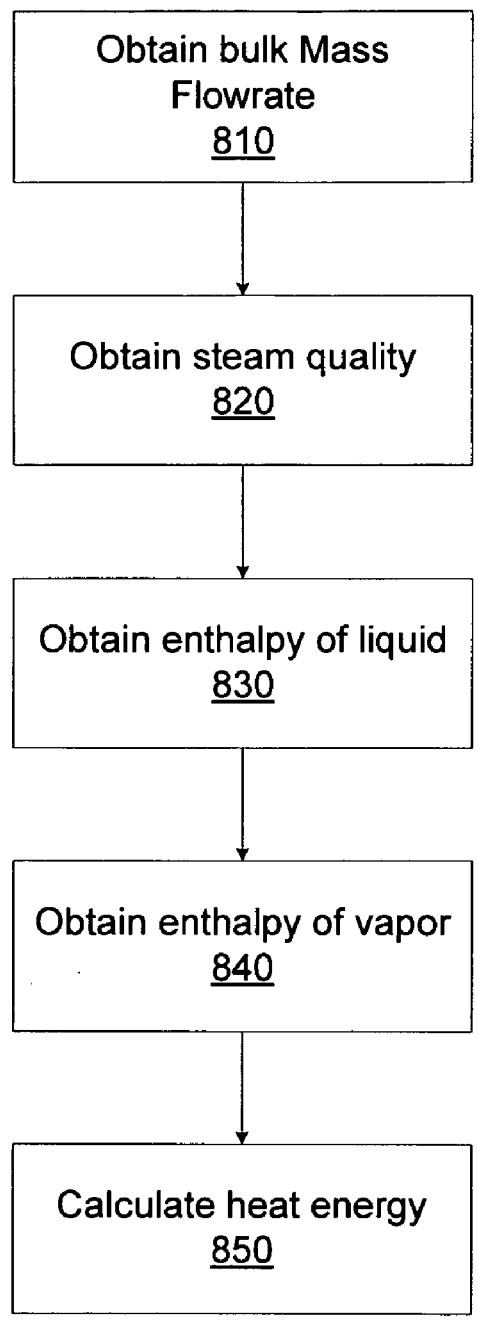
FIG. 8 is a flowchart describing a process for determining heat energy flow rate measurements.

FIG. 8 is a flowchart describing a process 800 for determining heat energy flow rate measurements using the steam quality and the mass flow rate. Process 800 may be implemented using, for example, one of the configurations illustrated in FIGS. 4-6.

As described above, a Coriolis flowmeter may be used to measure the bulk mass flow rate of the two-phase steam. Using the bulk mass flow rate, the steam quality, and information about the wet steam obtainable from a steam table, the heat energy flow rate of steam flowing into a well 160 may be calculated. Such a heat energy flow rate measurement, along with the mass flow rate, may provide an operator of the injection wells 160 with additional information helpful in optimizing the steam-injection process.

Accordingly, referring to FIG. 8, the bulk mass flow rate of the steam is obtained by a Coriolis flowmeter (810). The steam quality is calculated (820) as described above using a reading from a temperature or pressure sensor/transmitter, such as sensor 550 or 650, and a steam table such as the one shown in FIG. 3. The temperature or pressure is then used to calculate the enthalpy of the liquid phase (830) and the enthalpy of the vapor phase (840). Like the densities for the steam quality calculation, the enthalpies may be calculated by storing a steam table, for example, in a transmitter and looking up the appropriate property in the steam table. For instance, referring to the steam table of FIG. 3, if the temperature sensor associated with Coriolis flowtube 410 or temperature transmitter 550 indicates 360° F. (or if absolute pressure transmitter 650 indicates 153 psia) then the enthalpy of the liquid phase is calculated from the steam table of FIG. 3 as 332.3 BTU/lbm and the enthalpy of the vapor phase is calculated as 1194.4 BTU/lbm. Alternatively, the steam table information may be stored algorithmically and the algorithm may be used to obtain the enthalpies.

The enthalpies of the vapor and liquid phases, along with the bulk mass flow rate, and the steam quality are then used to calculate the heat energy flow rate of the steam (850). The following equation expresses the relationship between the heat energy flow rate $H_{total}$, bulk mass flow rate m, the vapor enthalpy $h_g$, liquid enthalpy $h_f$, and steam quality x.

$$H_{total} = m \cdot h_g \cdot x + m \cdot h_f \cdot (1-x)$$

Using the 360° F. example discussed above with 67% quality, and assuming a mass flow, m, of 20,000 lb/day:

$$H_{total} = 20,000(1194.4)0.67 + 20,000(332.3)(1-0.67)$$

$H_{total}$=18.2 million Btu per day.

Figure 9:
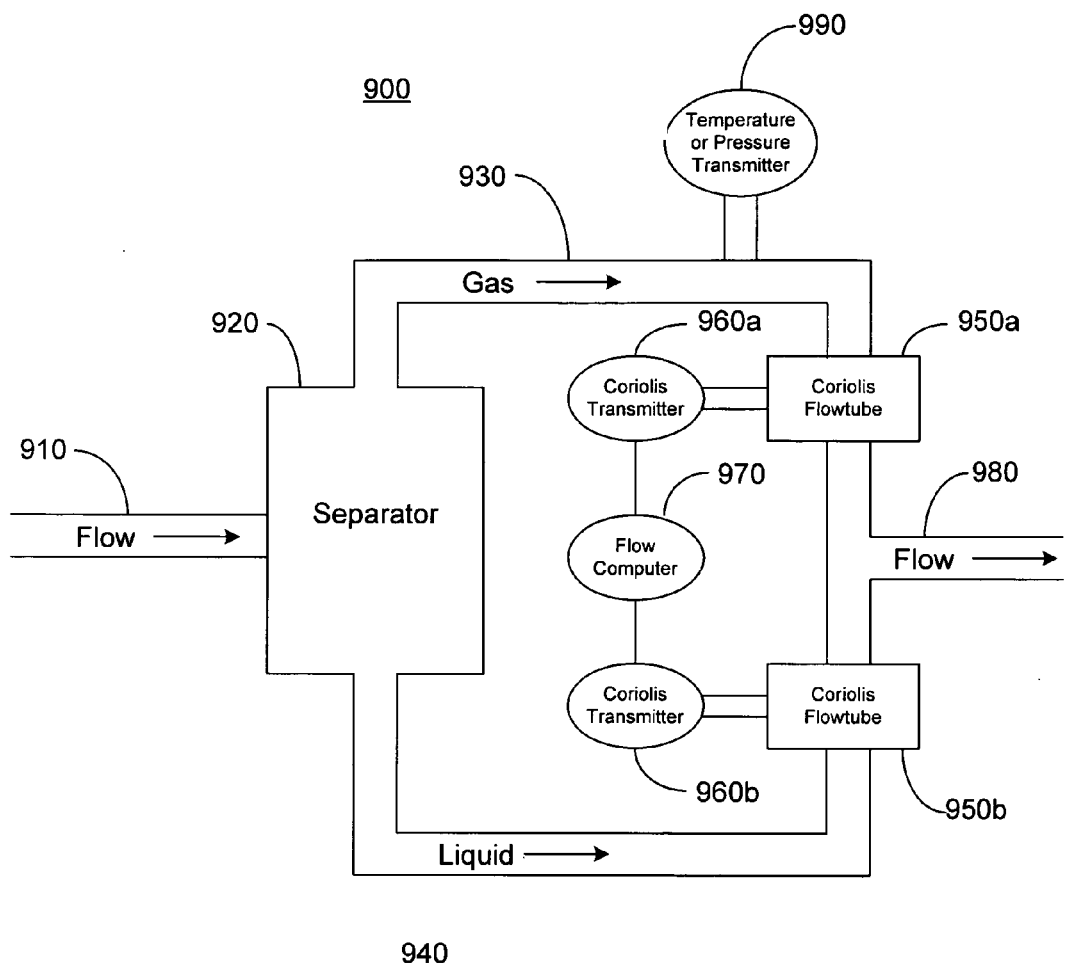
FIG. 9 is a block diagram of a steam measurement system used in conjunction with a gas/liquid separator.

FIG. 9 is a block diagram of a system 900 that includes a steam measurement system used in conjunction with a gas/liquid separator. In system 900, the two-phase, wet steam is separated to some extent by a separator 920. Such a configuration may be desirable in some circumstances. For instance, some Coriolis flowmeters do not accurately measure density and mass flow if the gas fraction (GVF or Gas Volume Fraction) is above a particular amount, for example, about 30%; or below a particular amount, for example, about 90%. An implementation using a partial or full separator also may allow a use of a temperature/pressure transmitter directly on a substantially pure gas phase of the two-phase steam.

Wet steam is input to a full or partial separator 920 by an input transport element 910. Separator 920 fully or partially separates the wet steam into a substantially gas flow and a substantially liquid flow. The substantially gas flow is output through a gas transport element 930, while the substantially liquid flow is output through a liquid transport element 940. A temperature or pressure transmitter 990 may be connected to gas transport element 930 for measuring the temperature or pressure of the substantially gas flow, which will be equal to the temperature or pressure of the substantially liquid flow. A Coriolis flowtube 950a and associated transmitter 960a also is connected to gas transport element 930. Similarly, a Coriolis flowtube 950b and associated transmitter 960b is connected to liquid transport element 940. After flowing through Coriolis flowtubes 950a and 950b, respectively, the substantially gas flow and the substantially liquid flow combine and are output through output transport element 980.

Coriolis flowtube 950a and transmitter 960a therefore can detect the bulk density of the substantially gas flow, while the Coriolis flowtube 950b and transmitter 960b can detect the bulk density of the substantially liquid flow. Coriolis transmitter 960a transmits the bulk density of the substantially gas flow to flow computer 970. Coriolis transmitter 960b also transmits the bulk density of the substantially liquid flow to flow computer 970. The mass flow rates of the substantially gas and liquid flows also may be measured by the respective Coriolis flowtube 950a or 950b and transmitter 960a and 960b. With the densities of the gas and liquid flows, and the temperature or pressures of the two flows, flow computer 970 can calculate the total steam quality, the total mass flow rate, and the total heat energy flow rate of the flow exiting through output transport element 980. To calculate the total mass flow rate, flow computer 970 adds the mass flow rates of each flow. To calculate the total steam quality and the total heat energy flow rate, flow computer 970 calculates the steam quality and heat energy flow rate of each flow, in a manner similar to that described above, and sums the values.

Figure 10:
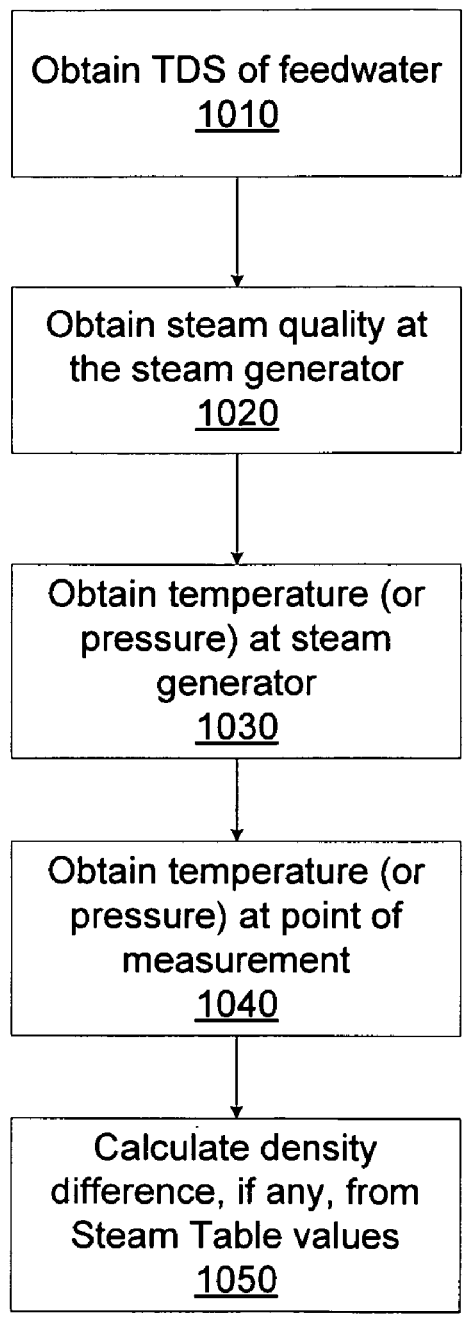
FIG. 10 is a flowchart describing a process for accounting for dissolved solids when determining steam quality measurements.

FIG. 10 is a flowchart describing a process for accounting for dissolved solids when determining steam quality measurements. This may be particularly useful when calculating steam quality measurements for low steam quality flows, such as, for example, flows that have 10-20% steam quality. The feed water used in steam generator 120 may be high in total dissolved solids (TDS), if it is, for example, pre-processed, produced water or ground water. As it passes through generator 120 and most of it turns to vapor, the remaining liquid becomes concentrated with TDS. For example, if the feed water is 2000 ppm TDS, and the generator puts out 80% quality steam, the liquid phase will concentrate to 10,000 ppm TDS. This will result in the liquid phase being denser by 0.62 lb/ft$^3$ than the steam tables indicate. The steam table of FIG. 3 is based on pure, distilled water, but a Coriolis flowmeter will measure the bulk density of the vapor and the liquid with the TDS.

Moreover, as the two-phase steam loses pressure from, for example, friction in the flow lines and pressure drops from valves and chokes, more of the liquid turns to vapor, concentrating the TDS in the liquid phase even further.

The steam quality actually increases with pressure drop, and with a constant enthalpy process this can be calculated by:

$$H_1 = H_2$$

$$(1-x_1)H_{1f} + x_1 H_{1g} = (1-x_2)H_{2f} + x_2 H_{2g}.$$

Where $x_1$ is the quality before, and $x_2$ is the quality after, and the various "H" terms are the enthalpies of the liquid and vapor (f and g, respectively) before and after. If we take our previous example of 80% quality steam at, say 440° F. (381.5 psia); and this drops to 360° F. (153 psia), then:

$$(1-0.8)419 + 0.8(1204.4) = (1-x_2)332.3 + 1194.4 x_2$$

$$x_2 = 0.83 \text{ or } 83\% \text{ quality.}$$

In this case, the liquid phase has concentrated the TDS by another 3% so the resulting TDS is now 10,309.3 ppm, or 0.64 lb/ft$^3$ denser than the steam tables.

In the case of FIG. 10, then, the TDS of the feed water, the steam quality at the generator, the temperature (or pressure) at the generator, and the temperature (or pressure) at the point of measurement are used to detect a measurement (e.g., density) difference, if any, from the steam table of FIG. 3. Such a difference can then be used to obtain accurate indications of steam quality and/or heat energy flow rate of the wet steam. The generator data can be communicated digitally to all measurement points as the generator conditions change, or can be manually input into the transmitter and/or flow computer.

In performing the above-described measurements and calculations, a static mixer may be placed upstream of the Coriolis flowmeter(s) (e.g., in FIG. 1). Such a static mixer may be instrumental in avoiding calculation issues related to, for example, slip velocities of the vapor and liquid (e.g., the velocities of the vapor and liquid relative to one another within the flow), and/or to different flow regimes of the flow (e.g., the manner in which the vapor and liquid are contained and flowing within the wet steam. For example, in one regime, the liquid may flow around a perimeter of the transport element (e.g., tube), with the vapor in the middle.

In another regime, the vapor may be dispersed as bubbles within the wet steam liquid phase). Alternatively, the static mixer may be avoided by accounting for these and other parameters during calculations, perhaps using examples and techniques discussed in, for example, the U.S. Provisional Application No. 60/452,934, titled Multiphase Coriolis Flowmeter and filed Mar. 10, 2003, which is hereby incorporated by reference.

A number of implementations have been described. Nevertheless, it will be understood that various modifications may be made.

What is claimed is:

1. A steam measurement system comprising:
    a Coriolis flowtube to receive a flow of wet steam, wherein a bulk density of the flow is determined based on a motion of the Coriolis flowtube;
    a sensor to determine a property of the flow of wet steam; and
    a computing device configured to calculate a steam quality of the flow from the bulk density and the property.

2. The steam measurement system of claim 1 wherein the property is a temperature of the flow and the sensor is a temperature sensor.

3. The steam measurement system of claim 2 wherein the temperature sensor is connected to the outside of the flowtube.

4. The steam measurement system of claim 2 wherein the temperature sensor is inserted into the flow of wet steam.

5. The steam measurement system of claim 1 wherein the property is a pressure of the flow and the sensor is a pressure sensor.

6. The steam measurement system of claim 1 wherein, to calculate the steam quality, the computing device is configured to calculate a density of a vapor phase of the flow from the property and to calculate a density of a liquid phase of the flow from the property.

7. The steam measurement system of claim 6 wherein the computing device includes a memory storing a steam table, the computing device configured to use the steam table to calculate the density of the vapor phase from the property and the density of the liquid phase from the property.

8. The steam measurement system of claim 6 wherein, to calculate the steam quality, the computing device is configured to use the bulk density, the density of the liquid phase, and the density of the gas phase to solve the following equation for the steam quality $$x: \frac{1}{\text{Bulk Density}} = \frac{x}{\text{Vapor Density}} + \frac{1-x}{\text{Liquid Density}}.$$

9. The steam measurement system of claim 1 wherein the computing device comprises a Coriolis transmitter.

10. The steam measurement system of claim 1 wherein the computing device comprises a flow computer.

11. A method comprising:
    passing a flow of wet steam through a vibrating flowtube associated with a Coriolis flowmeter, wherein the Coriolis flowmeter determines the bulk density of the flow of wet steam;
    obtaining a temperature or a pressure of the flow of wet steam; and
    calculating a steam quality of the flow from the bulk density and the temperature or pressure.

12. The method of claim 11 wherein obtaining a temperature or a pressure of the flow of wet steam comprises obtaining the temperature of the flow of wet steam.

13. The method of claim 12 wherein obtaining the temperature of the flow of wet steam comprises connecting a temperature sensor to the outside of the flowtube.

14. The method of claim 12 wherein obtaining the temperature of the flow of wet steam comprises inserting a temperature sensor into the flow of wet steam.

15. The method of claim 11 wherein obtaining a temperature or a pressure of the flow of wet steam comprises obtaining the pressure of the flow of wet steam.

16. The method of claim 11 wherein calculating the steam quality comprises:
    calculating a density of a vapor phase of the flow from the temperature or pressure; and
    calculating a density of a liquid phase of the flow from the temperature or pressure.

17. The method of claim 16 wherein calculating the density of the vapor phase of the flow or calculating the density of the liquid phase of the flow from the temperature or pressure comprises:
    storing a steam table; and
    using the steam table to calculate the density of the vapor phase of the flow or calculate the density of the liquid phase of the flow from the temperature or pressure.

18. The method of claim 16 wherein calculating the steam quality comprises solving the following equation for the steam quality x:

$$\frac{1}{\text{Bulk Density}} = \frac{x}{\text{Vapor Density}} + \frac{1-x}{\text{Liquid Density}}.$$

* * * * *